United States Patent [19]
Aslam et al.

[11] Patent Number: 5,130,448
[45] Date of Patent: Jul. 14, 1992

[54] SYNTHESIS OF 1-AMINOANTHRAQUINONE

[75] Inventors: Mohammad Aslam; Daniel A. Aguilar, both of Corpus Christi, Tex.

[73] Assignee: Hoechst Celanese Corporation, Somerville, N.J.

[21] Appl. No.: 654,850

[22] Filed: Feb. 12, 1991

[51] Int. Cl.$^5$ .................. C07C 725/34; C07C 2/68
[52] U.S. Cl. .................. 552/251; 552/208; 568/319
[58] Field of Search .............. 552/251, 208; 568/319, 568/31, 42; 585/464

[56] References Cited

U.S. PATENT DOCUMENTS

| | | | |
|---|---|---|---|
| 3,873,538 | 3/1975 | Oxford et al. | 260/247.2 R |
| 3,959,318 | 5/1976 | Torisu et al. | 260/369 |
| 3,966,774 | 6/1976 | Stoll et al. | 260/378 |
| 4,105,680 | 8/1978 | Chung | 260/378 |
| 4,328,161 | 5/1982 | Chung | 260/378 |
| 4,379,092 | 4/1983 | Devic | 260/369 |
| 4,804,501 | 2/1989 | James et al. | 260/369 |
| 4,894,482 | 1/1990 | Lindley et al. | 568/319 |
| 4,966,984 | 10/1990 | Devic | 552/208 |
| 5,041,616 | 8/1991 | Samner, Jr. | 568/319 |

OTHER PUBLICATIONS

"Synthesis of Chloro Derivatives of 2-Anthraquinonecarboxylic Acid", N. S. Dokunikhin et al, Scientific Research Institute of Organic Intermediates and Dyes, Translated from Zhurnal Obshchei Khimii, vol. 31, No. 12, pp. 3985-3987, Dec. 1961.

"Liquid-Phase Catalytic Oxidation of 3,5-Dimethyldiphenylmethane and Its Methyl-, Chloro-, and Nitro-Substituted Derivatives", Yu. V. Pozdnyakovich et al, Rubezhnoe Branch, Scientific-Research Institute of Organic Intermediates and Dyes, pp. 349-359, Translated from Zhurnal Organicheskoi Khimii, vol. 19, No. 2, pp. 398-403, Feb. 1983.

"Synthesis of Substituted 1,4,5-Trimethyldiphenylmethanes", Yu. V. Pozdnyakovich et al, Rubezhnoe Branch, Scientific-Research Institute of Organic Intermediates and Dyes, pp. 353-359, Translated from Zhurnal Organicheskoi Khimii, vol. 19, No. 2, pp. 403-411, Feb. 1983.

"Anthraquinone Derivatives", Kirk-Othmer Encyclopedia of Chemical Technology, vol. 2, pp. 716-719 and 725-728.

Primary Examiner—C. Warren Ivy
Assistant Examiner—Raymond Covington
Attorney, Agent, or Firm—S. D. Frenkel; D. R. Cassady

[57] ABSTRACT

1-Aminoanthraquinone (1-AAQ) is synthesized by the condensation of 2-substituted benzoic acid and xylene to yield 2-substituted-dimethylbenzophenone, subsequent oxidation of the methyl groups, ring closure to form a 1-substituted anthraquinone carboxylic acid, replacement of the 1-substituent with ammonia, and decarboxylation.

35 Claims, No Drawings

SYNTHESIS OF 1-AMINOANTHRAQUINONE

BACKGROUND OF THE INVENTION

The present invention relates to a novel synthetic route for the production of 1-aminoanthraquinones.

1-Aminoanthraquinone is a well known and important intermediate used in the preparation of colorants including dyes and pigments as well as other specialty chemicals. 1-Aminoanthraquinone is particularly useful as an intermediate in the prepartion of fiber-reactive dyes. Thus, in the past, most dyes were dispersed dyes which relied on surface properties such as static interaction to bond to a fabric. Presently, new fiber-reactive dyes which react with chemical sites on the fabric fibers have provided a significant improvement in the ability of the dye to remain bonded to the fabric. 1-Aminoanthraquinone is an intermediate for the formation of such fiber-reactive dyes. For example, 1-amino-4-bromoanthraquinone-2-sulfonic acid (Bromamine Acid), an important intermediate in a fiber reactive dye, can be formed by treatment of 1-aminoanthraquinone with oleum or chlorosulfonic acid to form the 1-aminoanthraquinone-2-sulfonic acid derivative which is then followed by treatment with bromine. This brominated compound can be subsequently reacted with another compound which can couple with the fabric fiber. Importantly, the chromophore, i.e., the 1-aminoanthraquinone, becomes part of the molecule which couples with the fabric fiber. It is important that the amino group be located on the 1-position of the anthraquinone inasmuch as the placement of the amino group on other positions of the anthraquinone yields a color body of a different color.

1-Aminoanthraquinone has been prepared by the reaction of anthraquinone with oleum in the presence of mercury to produce anthraquinone-1-sulfonic acid which, in turn, is reacted with ammonia. However, mercury is a known toxic chemical and thus, poses severe environmental problems with its use. In an alternative process to produce 1-aminoanthraquinone, anthraquinone is nitrated directly followed by reduction of the nitroanthraquinone. Unfortunately, direct nitration of anthraquinone yields a mixture of products including 1-, 2-, and dinitroanthraquinones which upon hydrogenation yield the corresponding aminoanthraquinone mixture. Consequently, the product which is formed subsequent to reduction yields more than one color body and intricate methods of separation must be used to obtain the pure 1-aminoanthraquinone. Not only with nitration, but with other processes which attempt to add a functional group which can be converted to an amino functional group, selectivity to the 1-position is marginal as other is2omers are formed or complicated process schemes are required to fix the amino group at the 1-position on the anthraquinone.

Accordingly, it is an object of the present invention to provide a commercially feasible and economical process for the selective production of 1-aminoanthraquinone and substituted derivatives thereof without the disadvantages of the prior art processes as mentioned above.

SUMMARY OF THE INVENTION

According to the invention, 1-aminoanthraquinone and substituted derivatives thereof are formed having the general formula:

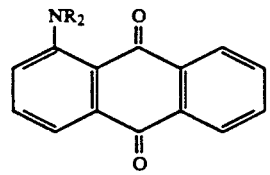

in which R represents hydrogen, alkyl, cycloalkyl, or aryl. The anthraquinone may be substituted as long as the substituents do not adversely affect the process for producing the 1-aminoanthraquinone as described below.

The invention involves a novel process scheme to form 1-aminoanthraquinone, which scheme includes a series of novel reactions and the formation of a novel intermediate compound mixture. Briefly, as depicted below 1-aminoanthraquinone and 1-aminoanthraquinone-carboxylic acid are prepared by a synthesis which involves the steps of (i) HF-catalyzed condensation of a 2-substituted benzoic acid or derivative thereof, (1) with xylene (2) to afford 2-substituted dimethylbenzophenone (3); (ii) air oxidation to afford 2-substituted benzophenonedicarboxylic acid (4); (iii) oleum-catalyzed ring closure to afford a mixture of 1-substituted anthraquinonecarboxylic acid isomers (5); (iv) ammonolysis to afford 1-aminoanthraquinonecarboxylic acid (6); and (v) decarboxylation to afford 1-aminoanthraquinone (7).

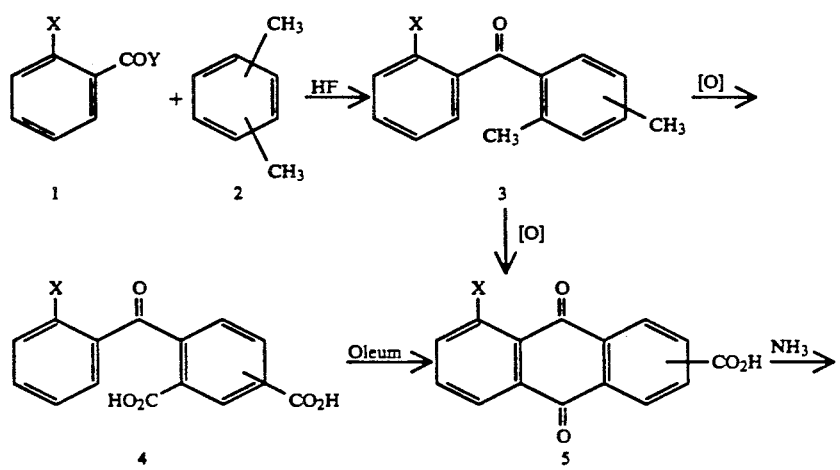

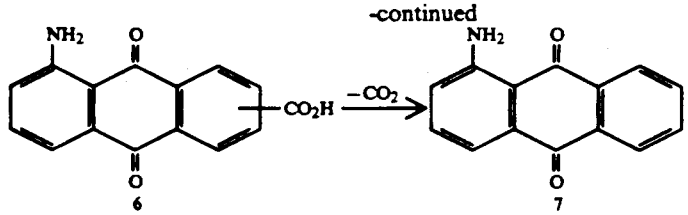

wherein X may be halogen, hydroxy, nitro, thioalkyl, alkoxy, or sulfonyl-containing group and Y may be OH, halogen, or 2-X benzoyloxy, where X has the same meaning as above.

The process scheme of this invention utilizes inexpensive starting materials, avoids toxic catalysts such as mercury used in the prior art and fixes the leaving group for substitution with amino at the beginning of the process to provide excellent selectivity to the 1-aminoanthraquinone without the need for purification or cumbersome reaction mechanisms to provide the desired selectivity.

DETAILED DESCRIPTION OF THE INVENTION

In the first step (i) of the process to form 1-aminoanthraquinone as in the present invention, a 2-substituted benzoic acid or derivative thereof depicted as compound 1 above is reacted with xylene in the presence of liquid HF. The benzoic acid derivative can be a benzoyl halide or benzoic anhydride. The substituent X represents a leaving group which is a group that can be substituted with an amino group to afford the 1-aminoanthraquinone. Typical leaving groups include the halogens, hydroxy, alkoxy, nitro and sulfonyl including organosulfonyl groups. The preferred leaving group is a halogen with the most preferred being chlorine. Since the leaving group is fixed at the 2-position of the benzoic acid or derivative compound used at the start of the process of this invention, 1-aminoanthraquinone can be selectively produced without the need for the separation of isomers. In the present invention, the 1-amino group is fixed by the use of the leaving group at the 2-position of the benzoic acid (or benzoic acid derivative as previously described) at the very start of the reaction scheme. The starting xylene designated as compound 2 above can be ortho-, meta- or para-xylene. Meta-xylene is preferred.

The condensation of the 2-substituted benzoic acid or benzoic acid derivative with xylene takes place in the presence of liquid HF. While additional solvent is not needed, a solvent which is inert to the reactants and the HF catalyst may be utilized. The amount of such additional solvent is not critical. Non-limiting examples of solvents include the halogenated solvents such as methylene chloride, chloroform, etc. For the reaction, the 2-substituted benzoic acid or derivative and the xylene are present in equal molar amounts, typically. A slight excess of xylene may be tolerated and may even be useful as a solvent. The product which is formed comprises 2-substituted-2', (3', 4' or 5')-dimethylbenzophenone which is designated as compound 3 in the reaction scheme described previously. The placement of the methyl group at the 3', 4' or 5' position of the formed benzophenone will depend on whether ortho-, meta- or para-xylene was reacted, respectively. The temperature of reaction can range from about 30°-100° C., preferably 40°-80° C. and most preferably about 50° C. Pressure is not critical and additional pressure other than that formed by the vapor of the solvents or the HF catalyst is not needed, although, not believed to be undesirable. Upon completion of the reaction, the HF can be vented from the reactor in the vapor state and collected and recycled, leaving the liquid product.

In step (ii) of the process, the 2-substituted-dimethyl benzophenone is oxidized to yield the 2-substituted benzophenone dicarboxylic acid which is designated as compound 4 in the process scheme described above. Any oxidation process which can successfully oxidize the methyl groups to carboxyl groups can be used in this step of the process. Liquid phase chemical oxidation agents such as alkali metal dichromates, e.g., potassium dichromate, sodium dichromate and potassium permanganate, etc. can be used. However, oxidation with chemical agents is not preferred. For one, it has been found that oxidation using chemical oxidizing agents does not provide very high yields of the desired product and, subsequent to reaction there is a problem of disposing of the chemical agents. The preferred method is the liquid phase air oxidation of the 2-substituted dimethyl benzophenone.

The air oxidation of the 2-substituted-dimethyl benzophenone to the corresponding dicarboxylic acid is preferably accomplished in air under pressure in acetic acid in the presence of a cobalt-manganese-bromide catalyst as described in U.S. Pat. No. 4,804,501 herein incorporated by reference. It has further been found that air oxidation of the 2-substituted-dimethyl benzophenone can result in direct formation of a small but significant amount of anthraquinonecarboxylic acid depicted as compound 5 in the above reaction scheme. Obviously, air oxidation may provide a substantial savings if the oleum cyclization can be deleted from the reaction scheme.

The weight ratio of 2-substituted dimethyl benzophenone to acetic acid is in the range of from about 1:1 to about 1:20, preferably in the range of from about 1:4 to about 1:20. The cobalt-manganese-bromide catalyst which is used has a mole ratio of cobalt to manganese of about 1.0:0.1 to about 1.0:10.0, and mole ratio of bromide to total metals of the catalyst is from 0.2:1.0 to about 20.0:1.0. Preferably, the mole ratio of cobalt-to-manganese is from about 1.0:0.1 to about 1.0:10.0, and the mole ratio of bromide to total metals of the catalyst is from about 3.0:1.0 to about 10.0:1.0. The process comprises oxidation of the 2-substituted dimethyl benzophenone at a temperature within the range of from about 75° C. to about 250° C. at a pressure of from about 1 to about 100 atmospheres.

An alternative oxidation catalyst which can be used is a zirconium-cobalt-manganese-bromide catalyst wherein the mole ratio of zirconium to cobalt is about 0.005:1.0 to about 0.20:1.0; the mole ratio of cobalt to manganese is from about 1.0:0.1 to about 1.0:10.0, and mole ratio of bromide to total metals of catalyst is from about 0.2:1.0 to about 20.0:1.0. Preferably, the mole ratio of zirconium to cobalt in the catalyst is from about 0.01:1.0 to about 0.10:1.0 and the mole ratio of cobalt-to-manganese is from about 1.0:0.1 to about 1.0:10.0 and the mole ratio of bromide to total metals of the catalyst is from about 3.0:1.0 to about 10.0:1.0.

In step (iii) of the process to form 1-aminoanthraquinone according to the present invention, ring closure of the 2-substituted benzophenone dicarboxylic acid is achieved by acid catalysis. Preferably, the ring closure to form the 1-substituted anthraquinone carboxylic acid (5) is done by reacting the 2-substituted benzophenone dicarboxylic acid with about 10 to 40% oleum in concentrated sulfuric acid. The temperature of the reaction can range from about room temperature to 120° C., preferably 60°-100° C. and most preferably from about 90°-95° C. The reaction should run from about 2 to about 6 hours.

It has been found, at least with respect to cyclization of the 2-substituted benzophenone 2',4'-dicarboxylic acid which results when utilizing meta-xylene in step (i) of the process, that this compound undergoes Hayashi rearrangement to afford a mixture of two dicarboxylic acids, the 2-substituted benzophenone 2',4'-dicarboxylic acid and the 2-substituted benzophenone-2',5'-dicarboxylic acid. Upon cyclization, what is formed is a mixture of 1-substituted anthraquinone carboxylic acid isomers in which the carboxyl group is located at the 6- or 7-position on the anthraquinone. The mixture comprises approximately a 50:50 ratio of the individual isomers. It is believed that a similar isomerization will occur upon cyclization of the 2-substituted benzophenone dicarboxylic acids which have been formed from ortho- or para-xylene at the beginning of the process scheme of this invention.

Although the use of oleum for ring closure is preferred, other known cyclization catalysts can be used. For example, sulfuric acid, polyphosphoric acid, HF or an HF/BF$_3$ catalyst at a temperature of about 50° C. to about 80° C. can also be utilized. Isomerization using this latter catalyst has also been found.

Step (iv) of the process of this invention is the ammonolysis of the 1-substituted anthraquinone carboxylic acid. The 1-substituted anthraquinone carboxylic acid is reacted with any amine of the formula RNH$_2$ wherein R can be hydrogen, alkyl, cycloalkyl and aryl. Since the anthraquinone which is formed during cyclization in Step (iii) of the present process contains a carboxylic acid moiety, the 1-substituted anthraquinone carboxylic acid is water soluble and the ammonolysis may take place in water. If desired, organic solvents may be included. However, the water solubility of the precursor formed in the present invention is a clear advantage over reaction mechanisms which require organic solvent systems for nitration. The reaction may take place in the presence of a copper catalyst, if desired. The use of the catalyst reduces the reaction time. However, less yield of the desired 1-aminoanthraquinone carboxylic acid results as other byproducts are formed. On the other hand, without the catalyst, the reaction times are relatively long but yields of the desired product are substantially higher than those achieved with the catalyst. Reaction temperatures are not overly critical with a typical temperature ranging from about 100°-150° C. Although not overly critical, it is important to note that a temperature which is too high may cause the desubstitution at the 1 position of the anthraquinone. Obviously, at too low a temperature, little or no reaction takes place.

The final step (v) of the process of this invention is the decarboxylation of the 1-aminoanthraquinone carboxylic acid. Decarboxylation is a known process and is typically achieved by heating the 1-aminoanthraquinone carboxylic acid in a solvent in the presence of a catalyst such as copper, iron, tin or zinc. Copper or copper oxide is the preferred catalyst in this invention. The solvents which can be used include n-methyl-pyrrolidone, pyridine, quinoline, lutidine, collidine, and acetic acid. Pyridine is preferred. The temperature of the reaction should be from about 200°-350° C. with a preferred range of about 230°-270° C.

The 1-aminoanthraquinones formed by the process of this invention can be used as intermediates for dyes for fabrics, dyes for hair, pigments, printing inks, electro-optical device colorants, photographic sensitizer, DNA binding, antitumor properties, and chromophoric compounds for determination of biological compounds.

The following examples illustrate the investigation of the individual reactions which form the process scheme of this invention. The examples are illustrative only and should not be construed as limiting the invention to the embodiments shown in such examples.

EXAMPLE 1

This example describes the HF-catalyzed condensation of o-chlorobenzoic acid with m-xylene.

2-Chlorobenzoic acid (1175 g, 7.5 mol) and m-xylene (875 g, 8.25 mol) were charged in an 8 liter Hastelloy-C autoclave and anhydrous HF (4500 g, 225 mol) was added. The reaction mixture was heated to 50° C. and stirred for 3.5 hours. After cooling to room temperature, most of the HF was vented through a KOH scrubber and the reactor purged with nitrogen. The reactor contents were added to ice and the resulting solution was neutralized with 45% KOH to a pH=7.0. The organic layer was separated, washed with water, dried over anhydrous magnesium sulfate and the magnesium sulfate removed via filtration to afford an oil (1602 g). The aqueous layer was extracted with ethyl acetate (1 L). Ethyl acetate extract was dried over anhydrous magnesium sulfate, filtered and concentrated to afford an oil (46 g). The two oily products were combined and distilled under reduced pressure (b.p. 138°-140° C. at 0.025 mm) to afford the product of 2-chloro-2',4'-dimethylbenzophenone (98% pure) (1560 g, 83% yield). The reaction proceeded smoothly with high conversion and with the formation of small quantities, e.g., 1 to 2 wt. % of other isomers of the product.

The HF-catalyzed condensation of 2-chlorobenzoic acid with p-xylene was also investigated. Condensation was carried out at 60° C. for 4.5 hours. 2-chloro-2',5'-dimethylbenzophenone product was isolated in 55% yield. Upon repeating the reaction at 80° C. for 4.5 hours, the conversion was slightly increased to afford the product in 60% yield. The results appear to show that p-xylene is not as reactive as m-xylene in this reaction.

EXAMPLE 2

This example illustrates the oxidation of 2-chloro-2',4'-dimethylbenzophenone.

A 1.0 Kg sample of 2-chloro-2',4'dimethylbenzophenone was subjected to air-oxidation at a temperature of about 90° C. in a bubblertype column to provide (97%) 2-chloro-2',4'benzophenone dicarboxylic acid and (2%) of 1-chloroanthraquinone carboxylic acid. Minimum yield was estimated to be 78%.

Oxidation of a small sample of 2-chloro-2',4'dimethylbenzophenone with potassium dichromate and potassium permanganate afforded the dicarboxylic acid in 50% yield. Replacement of potassium dichromate with sodium dichromate in this reaction gave a lower (36%) yield of the dicarboxylic acid. Similar oxidation of with alkaline potassium permanganate in the presence of a phase transfer catalyst (cetyltrimethylammonium bromide) afforded the dicarboxylic acid in a low yield (17%).

EXAMPLE 3

This example illustrates the oleum-catalyzed ring closure of the 2-chloro-benzophenonedicarboxylic acid to 1-chloro anthraquinonedicarboxylic acid.

To a 3 liter, round bottomed flask equipped with a condenser, a thermometer and a stirrer, 2-Chloro-2',4'or (2',5')-benzophenonedicarboxylic acid, conc. sulfuric acid (98%) and 20% oleum were added. See Table 1 for a description of starting materials and proportions of reactants. The reaction mixture was heated to 90° C. and stirred for 4.5 hours in all cases. Ice/water (850 mL) was slowly added to the reaction mixture and the product precipitated as a light green solid. The solid was filtered, washed with 70% sulfuric acid (2100 mL) and water (20 l) until the washings were not very acidic (pH>2). The solid was dried in vacuum oven at 60°–80° C. for 2 days to afford the product. See Table I for product yields.

The product formed in each case was a mixture of 1-chloroanthraquinone (-6- and -7-) carboxylic acid. Apparently the starting material undergoes Hayashi Rearrangement to afford a mixture of two dicarboxylic acids 2-chloro-benzophenone 2',(4'and 5')dicarboxylic acids. The two acids upon cyclization gave the corresponding anthraquinones.

verted to 1-aminoanthraquinone carboxylic acid without significant formation of anthraquinone-2-carboxylic acid (AQCA).

The reaction of 1-CAQCA with aqueous ammonia in the presence of 1 mol equivalent of NaOH at 138°–140° C. for ~30 hours (Exper. No. 6) affords 1-AAQCA. The reaction proceeded with 98% conversion. 1-AAQCA was isolated in 76% yield (based on the combined response factors for 1-AAQ-6-CA and 1-AAQ-7-CA). The product also contained anthraquinone-2-carboxylic acid (AQCA) (4.1%) and a purple compound (5%). The purple compound and the two isomers (1-AAQ-6-CA and 1-AAQ-7-CA) were separated via preparative HPLC. The purple compound was characterized as diaminoanthraquinonecarboxylic acid (DAAQCA).

The 1-CAQCA was also reacted with concentrated (28–30%) aqueous ammonia in the presence of potassium carbonate and air (100 psig) for 30 hours. After acidification of the aqueous reaction mixture with dilute acid, for example HCl or $H_2SO_4$, to a pH of about 1–4, a reddish brown solid was precipitated. The solid was isolated by filtration, washed with water, and dried in a vacuum oven at about 70° C. and 50 mm Hg (Exper. No. 7). The reaction proceeded with 95% conversion. 1-AAQCA was isolated in 90% yield. Small amounts of AQCA (1.1%) and DAAQCA (6%) were also formed in this reaction.

Ammonolysis with anhydrous ammonia in 1,2-dimethoxyethane at 140° C. for 3.5 hours proceeded with 49% conversion and low (~8%) 1-AAQCA yield (Exper. No. 11). Ammonolysis of 1-CAQCA in DMF at 140° C. for 5 hours proceeded with 97% conversion but low (3%) 1-AAQCA yield (Exper. No. 17). A significant amount (30%) of DAAQCA was the major impurity in this reaction. Reaction with ammonia in metha-

TABLE I

Synthesis of 1-Chloroanthraquinonecarboxylic Acids (1-CAQCA) from 2-Chlorobenzophenonedicarboxylic Acids (CBDA).

| Exper. No. | CBDA (g. mol) | 98% $H_2SO_4$ mL | 20% Oleum mL | Time (h) | Temp (°C.) | Yield[c] (g) | Yield[d] mol. | Conv. (%) | Yield (%) 1-CAQCA |
|---|---|---|---|---|---|---|---|---|---|
| 1[a] | 121.6, 0.4 | 400 | 200 | 4.5 | 90 | 108.0 | 0.38 | 100 | 94.0 |
| 2[b] | 243.3, 0.8 | 800 | 400 | 4.5 | 90 | 218.2 | 0.73 | 100 | 91.0 |
| 3[b] | 243.2, 0.8 | 800 | 400 | 4.5 | 90 | 217.0 | 0.74 | 100 | 92.0 |
| 4[b] | 121.8, 0.8 | 400 | 200 | 4.5 | 90 | 110.0 | 0.36 | 98 | 89.0 |
| 5[a] | 121.8, 0.8 | 400 | 200 | 4.5 | 90 | 107.0 | 0.36 | 100 | 91.0 |

[a]2-Chlorobenzophenone-2',5'-dicarboxylic acid was used as starting material.
[b]2-Chlorobenzophenone-2',4'-dicarboxylic acid was used as starting material.
[c]Yield of the crude product.
[d]Moles of pure products determined after HPLC-analysis.

Cyclization of 2-chlorobenzophenone 2',4'dicarboxylic acid (15.2 g) to 1-chloroanthraquinone carboxylic acids was also carried out in $HF/BF_3$ at 60° C. for 3 hours. After removal of $HF/BF_3$ by nitrogen purge, and neutralization of the reaction mixture using aqueous KOH, a brown solid (4.0 g) was isolated. LC-analysis of the solid revealed it to contain the mixture as described above (48%), corresponding to a 13% yield. C-NMR spectrum of the solid revealed the two isomers were present in approximately 2:1 ratio.

EXAMPLE 4

Ammonolysis of 1-chloroanthraquinonecarboxylic Acid (1-CAQCA) was investigated using aqueous ammonia for the synthesis of 1-aminoanthraquinone-6-and -7-carboxylic acids (1-AAQCA). The results and process conditions are summarized in Table II. It was found that in the absence of a copper catalyst, 1-chloroanthraquinone carboxylic acid could be connol at 140° C. was attempted. Analysis of a sample obtained after 5 hours suggested a very slow reaction and significant accumulation of unwanted products. At this point the reaction was terminated.

Ammonolysis of 1-CAQCA with anhydrous ammonia at 65° C. for 4 hours was unsuccessful and unreacted 1-CAQCA was recovered. Reaction of 1-CAQCA with anhydrous ammonia at a high pressure (1000 psig starting pressure, with $N_2$) at 120° C. for 3 hours gave a very low yield (Exper. No. 12). Ammonolysis with anhydrous ammonia in o-dichlorobenzene at 125° C. for 3.5 hours was unsuccessful (Exper. No. 9). Again, unreacted starting material was recovered.

It was observed that the rate of ammonolysis increased significantly with the use of copper catalysts. Ammonolysis of 1-CAQCA with Cu(O), Cu(I) and Cu(II) in ~20% aqueous ammonia afforded 1-AAQCA in 66-73% isolated yield. The actual yield in these reactions may be 10-15% higher than the isolated yield, due to the loss of material removed as samples during the reaction. These reactions proceeded with 97-99% conversion in 4-6 hours. AQCA was the main impurity (4-6%).

TABLE II

Synthesis of 1-Aminoanthraquinonecarboxylic Acids (1-AAQCA) from 1-Chloroanthraquinonecarboxylic Acids (1-CAQCA).

| Exper. No. | 1-CAQCA (g,mmol) | Base (g) | Catalyst (g) | $N_2$/Air psig | Solvent (ml) | Aq.$NH_3$ 28% (mL) | Temp (°C.) | Time (h) | Total wt. (g) |
|---|---|---|---|---|---|---|---|---|---|
| 1 | 15,52 | — | — | $N_2$, 50 | — | 150 | 140 | 26 | 13.9 |
| 2 | 15,52 | — | — | Air, 50 | — | 150 | 140 | 24 | 13.6 |
| 3 | 15,52 | — | — | Air, 50 | $H_2O$, 75 | 75 | 140 | 48 | 13.3 |
| 4 | 30,105 | — | — | $N_2$, 50 | — | 300 | 140 | 44 | 26.3 |
| 5 | 45,157 | — | — | $N_2$, 50 | — | 400 | 140 | 38 | 39.3 |
| 6 | 80,280 | NaOH, 11.2 | — | $N_2$, 50 | — | 800 | 140 | 30 | 70.5 |
| 7 | 140,469 | $K_2CO_3$, 61 | — | Air, 100 | — | — | 140 | 30 | 124.1 |
| 8 | 10,34 | — | — | Air, 100 | — | $100^b$ | 140 | 11 | 6.0 |
| 9 | 10,34 | — | — | Air, 100 | $DCB^d$, 100 | $30^e$ | 125 | 3.5 | 13.2 |
| 10 | 5,17 | — | $AgNO_3$ 0.15 | $N_2$, 85 | — | 100 | 140 | 5 | 4.2 |
| 11 | 10,34 | — | — | $N_2$, 65 | DME, 100 | $30^e$ | 140 | 3.5 | 8.9 |
| 12 | 5,17 | — | — | $N_2$, 1000 | — | $75^e$ | 120 | 1.5 | 3.6 |
| 13 | 5,17 | — | — | $N_2$, 1000 | — | 75 | 140 | 4 | 4.0 |
| 14 | 5,17 | $NaHCO_3$, 2.0 | MgO/CuO 0.04/0.07 | $N_2$, 80 | $H_2O$, 25 | 50 | 140 | 4 | 4.0 |
| 15 | 5,17 | $NaHCO_3$, 2.0 | MgO, 0.04 | $N_2$, 80 | $H_2O$, 25 | 50 | 140 | 5 | 4.3 |
| 16 | 5,17 | $NaHCO_3$, 2.0 | $CuCl_2$, 0.15 | $N_2$, 80 | $H_2O$, 25 | 50 | 140 | 4 | 4.4 |
| 17 | 5,17 | $NaHCO_3$, 7.7 | — | Air, 100 | DMF, 100 | $20^e$ | 140 | 5 | 2.0 |
| 18 | 5,17 | $NaHCO_3$, 7.7 | $CuWO_4$, 0.28 | $N_2$, 80 | $H_2O$, 25 | 50 | 140 | 4.5 | 4.0 |
| 19 | 5,17 | $NaHCO_3$, 7.7 | CuCl, 0.09 | $N_2$, 80 | $H_2O$, 25 | 50 | 140 | 4.5 | 4.4 |
| 20 | 5,17 | $NaHCO_3$, 7.7 | NiOAC, 0.3 | $N_2$, 80 | $H_2O$, 25 | 50 | 140 | 4.5 | 4.2 |
| 21 | 5,17 | $NaHCO_3$, 7.7 | Cu, 0.06 | $N_2$, 80 | $H_2O$, 25 | 50 | 140 | 4 | 4.0 |
| 22 | 5,17 | $NaHCO_3$, 7.7 | Cu, 0.06 | $N_2$, 80 | $H_2O$, 25 | 50 | 140 | 4.5 | 4.3 |
| 23 | 5,17 | $Na_2CO_3$, 3.7 | $CuCl_2$, 0.15 | $N_2$, 80 | $H_2O$, 25 | $50^f$ | 140 | 4.5 | 4.0 |
| 24 | 5,17 | $NaHCO_3$, 7.7 | $CuCl_2$, 0.15 | $N_2$, 80 | $H_2O$, 25 | $50^g$ | 140 | 5 | 4.0 |
| 25 | 5,17 | $NaHCO_3$, 7.7 | $CuOAc_2/MnAc_2$ 0.18/0.26 | $N_2$, 80 | $H_2O$, 25 | $50^f$ | 140 | 4 | 4.0 |
| 26 | 5,17 | $NaHCO_3$, 7.7 | $CuCl_2$, 0.15 | $N_2$, 80 | $H_2O$, 25 | 50 | 130 | 6 | 4.1 |
| 27 | 5,17 | $NaHCO_3$, 7.7 | $CuCl_2$, 0.075 | $N_2$, 80 | $H_2O$, 25 | 50 | 140 | 4 | 4.0 |
| 28 | 5,17 | $NaHCO_3$, 7.7 | $CuCl_2$, 0.075 | $N_2$, 80 | $H_2O$, 25 | 50 | 140 | 4 | 4.5 |
| 29 | 5,17 | $NaHCO_3$, 7.7 | $CuCl_2$, 0.03 | $N_2$, 80 | $H_2O$, 25 | 50 | 140 | 5 | 4.0 |
| 30 | 5,17 | $NaHCO_3$, 7.7 | $CuCl_2$, 0.075 | $N_2$, 80 | — | $75^b$ | 140 | 4 | 4.2 |
| 31 | 5,17 | $NaHCO_3$, 7.7 | EDTACu, 0.36 | $N_2$, 80 | $H_2O$, 25 | 50 | 140 | 4.0 | |

| Exper. No. | Conv. % | 1-AAQCA % | AQCA % | DAAQCA % | Unkn. % | 1-AAQCA Yield (%)$^a$ |
|---|---|---|---|---|---|---|
| 1 | 99 | 85 | 3.5 | 8.0 | 2.5 | 85 |
| 2 | 100 | 82 | 1.3 | 7.0 | 10.0 | 80 |
| 3 | 97 | 87 | 1.8 | 2.0 | 5.0 | 83 |
| 4 | 98 | 83 | 1.2 | 6.0 | 5.0 | 78 |
| 5 | 99 | 80 | 3.9 | 9.0 | 3.0 | 75 |
| 6 | 98 | 81 | 4.1 | 4.0 | 4.0 | 76 |
| 7 | 95 | 91 | 1.1 | 6.0 | 3.0 | 90 |
| 8 | 99 | 74 | 1.6 | 3.0 | 4.5 | $50^c$ |
| 9 | — | 0.0 | 0.0 | 0.0 | 0.0 | 0 |
| 10 | 44 | 49.5 | 0.0 | 0.0 | 4.0 | 46 |
| 11 | 49 | 7.8 | 23.0 | 23.0 | 7.5 | 8 |
| 12 | 40 | 3.6 | 2.2 | 0.0 | 11.5 | 3 |
| 13 | 40 | 29.8 | 1.9 | 0.0 | 5.0 | 31 |
| 14 | 99 | 78.6 | 4.3 | 4.3 | 5.5 | 70 |
| 15 | 55 | 41.9 | 4.0 | 1.5 | 4.5 | 43 |
| 16 | 100 | 74.6 | 6.0 | 4.9 | 6.0 | 77 |
| 17 | 97 | 6.3 | 0.7 | 29.5 | 6.0 | 3 |
| 18 | 99 | 74.3 | 6.7 | 0.0 | 8.0 | 76 |
| 19 | 99 | 70.7 | 5.9 | 7.0 | 6.0 | 73 |
| 20 | 31 | 26.0 | 2.1 | 0.0 | 6.0 | 24 |
| 21 | 99 | 76.2 | 8.4 | 0.0 | 11.0 | 68 |
| 22 | 97 | 69.3 | 9.6 | 0.0 | 9.0 | 67 |
| 23 | 95 | 64.0 | 11.3 | 0.0 | 10.0 | 57 |
| 24 | 98 | 66.7 | 13.7 | 1.7 | 8.0 | 60 |
| 25 | 96 | 81.5 | 6.9 | 7.4 | 4.0 | 73 |
| 26 | 92 | 75.6 | 5.1 | 1.7 | 5.0 | 69 |
| 27 | 98 | 77.9 | 7.6 | 2.0 | 6.0 | 70 |
| 28 | 97 | 75.5 | 7.4 | 2.0 | 6.0 | 76 |
| 29 | 95 | 73.1 | 9.3 | 2.1 | 7.0 | 65 |
| 30 | 99 | 86.0 | 6.5 | 4.5 | 5.0 | 81 |

TABLE II-continued

| | 31 | 99 | 86.1 | 6.4 | 1.3 | 4.0 | 77 |
|---|---|---|---|---|---|---|---|

*Yield was determined on the basis of response factor analysis via HPLC.
*48% aqueous ammonia was used in this reaction.
*Product was lost due to incomplete acidification.
*o-Dichlorobenzene.
*Grams of anhydrous ammonia was used.
/Hydrogen peroxide (0.2 g) was also added.
*Sodium sulfite (0.3 g) was also added.

EXAMPLE 5

Decarboxylation of 1-Aminoanthraquinone carboxylic Acid (1-AAQCA).

Process conditions and product yields are shown in Table III. The decarboxylation of 1-AAQCA was carried out in several solvents, e.g., N-methylpyrrolidone, pyridine, quinoline and acetic acid. The best results were obtained in pyridine. When decarboxylation of 1-AAQCA was carried out with 5 mol % of copper powder in pyridine at 260° C. for 2.5 hours, complete conversion was observed. Distillation of the crude product afforded 1-AAQ in 64% yield. We were unable to decarboxylate 1-AAQCA in pyridine alone, without a copper catalyst. Decarboxylation of 1-AAQCA in quinoline using 5 mol % of copper powder gave 1-aminoanthraquinone (1-AAQ) in 65% yield.

TABLE III

Synthesis of 1-Aminoanthraquinone (1-AAQ) from 1-Aminoanthraquinonecarboxylic Acids (1-AAQCA)

| Exper. No. | 1-AAQCA (g, mmol) | Catalyst (g, mmol) | Solvent (mL) | Temp$^a$ (°C.) | Temp (h) | Total wt. (g) | Conv. (%) | 1-AAQ (mmol) | 1-AAQ Yield (%)$^d$ |
|---|---|---|---|---|---|---|---|---|---|
| 1 | 5.0, 18.7 | CuO (0.15, 1.9) | Quin. (10) | 230 | 56.5 | 3.1$^b$ | 100 | 8.2 | 44 |
| 2 | 5.0, 18.7 | Cu (0.25, 3.9) | Quin. (50) | 260 | 2.0 | 2.5 | 100 | 7.3 | 65 |
| 3 | 10.0, 37.5 | Cu (0.5, 7.8) | Quin. (50) | 260 | 2.5 | 7.8 | 100 | 19.9 | 57 |
| 4 | 5.0, 18.7 | Cu (0.25, 3.9) | Pyri. (50) | 260 | 1.0 | 4.8$^c$ | 40 | 7.1 | 38 |
| 5 | 4.8, 18.0 | Cu (0.25, 3.9) | Pyri. (75) | 260 | 2.5 | 3.8$^c$ | 100 | 11.4 | 64 |
| 6 | 5.0, 18.7 | No catalyst | Pyri. (75) | 260 | 2.0 | — | 0.0 | 0.0 | 0.0 |
| 7 | 5.3, 19.8 | CuSO$_4$ (0.52, 2.0) | Pyri. (75) | 250 | 5.5 | 4.6 | 99 | 11.8 | 59 |
| 8 | 5.3, 16.1$^e$ | Cu (0.16, 2.5) | Pyri. (75) | 250 | 2.0 | 4.6$^c$ | 100 | 12.4 | 77 |
| 9 | 5.3, 16.1$^e$ | CuO (0.2, 2.5) | Pyri. (75) | 250 | 2.0 | 4.5$^c$ | 100 | 11.5 | 71 |
| 10 | 5.3, 17.4$^f$ | Cu (0.25, 3.9) | Pyri. (75) | 250 | 2.5 | 4.5$^c$ | 100 | 12.4 | 71 |
| 11 | 5.0, 16.4$^f$ | CuO (0.25, 3.1) | Quin. (20) | 238 | 6.0 | 3.8 | 100 | 10.2 | 62 |

$^a$Decarboxylations were carried out in a sealed autoclave under N$_2$ pressure. Quinoline runs were carried out at atmospheric pressure.
$^b$In quinoline runs the product is isolated by drowning the reaction mixture in dil. HCl followed by filtration of the product.
$^c$In pyridine runs, the product was isolated after removing the pyridine in-vacou.
$^d$Yield was determined on the basis of response factor analysis via HPLC.
$^e$91% pure 1-AAQCA was used.
$^f$88% pure 1-AAQCA was used.

EXAMPLE 6

This example investigated the reaction of step (i) of the present process using 2-nitro- benzoic acid as the starting material.

2-Nitrobenzoic acid (16.7 g, 0.1 mol) and m-xylene (11.7 g, 0.11 mol) were charged in a 300 cc Hastelloy-C autoclave. The reaction mixture was heated to 50° C. and stirred for 3 hours. Most of the HF was vented through a KOH scrubber and the product was transferred to a flask containing ice (100 g). The contents of the flask were neutralized to a pH=7. A brown solid (11.5 g) precipitated which was removed via filtration and discarded. The filtrate was extracted with ethyl acetate (2×100 mL). The ethyl acetate layer was dried and concentrated to afford the product (94% pure) (9.7 g, 35% yield) of 2-nitro-2',4'dimethyl benzophenone. A small portion (5.0 g) of the product was purified via Kugelrohr distillation to afford a yellow solid (4.2 g); m.p. 78°-80° C.

EXAMPLE 7

The formation of 2-hydroxy-2',4'-dimethylbenzophenone.

Salicylic acid (13.8 g, 0.10 mol) and m-xylene (15.9 g, 0.15 mol) were charged in a 300 cc Hastelloy-C autoclave where anhydrous HF (80.0 g, 4.0 mol) was added at −30° C. The reaction mixture was heated at 60° C. and stirred for 4 hours. After cooling to room temperature, most of the HF was vented through a KOH scrubber and the reactor purged with nitrogen. The reaction mixture was extracted with ethyl acetate and neutralized to a pH=7.0 with 45% KOH. The water layer was separated, acidified to a pH=3.0 with 45% HCl and extracted with ethyl acetate (2×150 ml). The ethyl acetate extracts were added to the organic layer. The organic layer was separated, washed with water (2×200 ml), dried over magnesium sulfate, filtered and concentrated in vacuo to afford a tan solid (20.0 g, 79% yield). A conversion of 80% was observed.

Under similar conditions, the HF catalyzed condensation of salicylic acid with p-xylene proceeded with a 35% conversion and 18% yield.

EXAMPLE 8

HF-catalyzed condensation of anthranilic acid with m-xylene for the production of 2-amino-2',4'-dimethylbenzophenone was also attempted. We didn't observe any reaction as unreacted anthranilic acid was recovered.

What is claimed is:

1. A process for producing a dimethylbenzophenone comprising condensing a 2-substituted benzoic acid with xylene in the presence of hydrogen fluoride.

2. The process of claim 1 wherein the condensation is carried out at temperature ranging from about 30° C. to about 100° C.

3. The process of claim 2 wherein the temperature is within the range of about 40° C. to about 80° C.

4. The process of claim 1 wherein the substituent of said 2-substituted benzoic acid is selected from the group consisting of halogen, hydroxy, alkoxy, thioalkyl, nitro and sulfonyl-containing groups.

5. The process of claim 4 wherein said substituent is halogen.

6. The process of claim 5 wherein said halogen is chlorine.

7. The process of claim 4 wherein the xylene is meta-xylene and the product is 2-substituted-2',4'-dimethylbenzophenone.

8. The process of claim 4 wherein the xylene is para-xylene and the product is 2-substituted-2',5'-dimethylbenzophenone.

9. The process of claims 7 or 8 wherein said substituent is halogen.

10. The process of claim 9 wherein said substituent is chlorine.

11. The process of claim 4 wherein said substituent is hydroxy.

12. The process of claims 7 or 8 wherein said substituent is hydroxy.

13. The process of claim 4 wherein said substituent is nitro.

14. The process of claims 7 or 8 wherein said substituent is nitro.

15. A process for preparing 1-aminoanthraquinones from 2-substituted benzoic acid or a 2-substituted benzoic acid derivative and xylene which comprises the steps of (i) condensing 2-substituted benzoic acid or benzoic acid derivative with xylene in the presence of hydrogen fluoride for a period of time sufficient to obtain a 2-substituted dimethylbenzophenone; (ii) air oxidizing said 2-substituted dimethylbenzophenone in the presence of a cobalt-manganese-bromide catalyst for a period of time sufficient to obtain a 2-substituted benzophenone-dicarboxylic acid; (iii) contacting said benzophenonedicarboxylic acid with an acid for a period of time sufficient to obtain a 1-substituted anthraquinone-carboxylic acid; and (iv) contacting said anthraquinonecarboxylic acid with ammonia or an amine of the formula $RNH_2$ wherein R is hydrogen, alkyl, cycloalkyl or aryl for a period of time sufficient to obtain a 1-amino-anthraquinonecarboxylic acid.

16. The process of claim 15 further comprising (v) decarboxylating said 1-aminoanthraquinonecarboxylic acid to obtain 1-aminoanthraquinone.

17. The process of claim 16 wherein steps (iv) and (v) are carried out in the presence of a copper catalyst.

18. The process of claim 15 wherein step (iv) is carried out in the absence of a catalyst.

19. The process of claim 15 wherein said air oxidation of 2-substituted dimethylbenzophenone affords 1-substituted anthraquinonecarboxylic acid.

20. The process of claim 15 wherein said benzophenone dicarboxylic acid is contacted in step (iii) with a strong acid catalyst.

21. The process of claim 20 wherein said strong acid catalyst is selected from the group consisting of oleum, sulfuric acid, phosphoric acid, HF, and $HF/BF_3$.

22. The process of claim 20 wherein said strong acid is oleum in concentrated sulfuric acid.

23. The process of claim 15 wherein said xylene is meta-xylene.

24. The process of claim 15 wherein said xylene is para-xylene.

25. The process of claim 15 wherein the substituent at the 2-position of said 2-substituted benzoic acid is selected from the group consisting of halogen, hydroxy, alkoxy, nitro and sulfonyl-containing groups.

26. The process of claim 25 wherein said substituent is halogen.

27. The process of claim 26 wherein said halogen is chlorine.

28. The process of claim 25 wherein said substituent is hydroxy.

29. The process of claim 25 wherein said substituent is nitro.

30. The process of claim 15 wherein said anthraquinone carboxylic acid in step (iv) is contacted with aqueous ammonia.

31. The process of claim 16 wherein the decarboxylation of 1-aminoanthraquinonecarboxylic acid is done in a nitrogen-containing aromatic heterocyclic solvent.

32. The process of claim 31 wherein said nitrogen-containing aromatic heterocyclic solvent is selected from the group consisting of quinoline, pyridine, lutidine, and collidine.

33. The process of claim 32 wherein said solvent is quinoline or pyridine.

34. The process of claim 16 wherein the decarboxylation is done at temperatures ranging from about 220° C. to about 280° C.

35. The process of claim 16 wherein the decarboxylation is done at temperatures ranging from about 250° C. to about 260° C.

* * * * *